United States Patent [19]

Maignan et al.

[11] Patent Number: 4,810,694

[45] Date of Patent: Mar. 7, 1989

[54] BENZONORBORNENE DERIVATIVES PROCESS, FOR THEIR PREPARATION AND MEDICINAL AND COSMETIC COMPOSITIONS COMPRISED THEREOF

[75] Inventors: Jean R. Maignan, Tremblay Les Gonesse; Braham Shroot, Antibes; Serge A. Restle, Aulnay Sous Bois, all of France

[73] Assignee: Centre International de Recherches Dermatologiques (C.I.R.D.), Valbonne, France

[21] Appl. No.: 817,605

[22] Filed: Jan. 10, 1986

[30] Foreign Application Priority Data

Jan. 10, 1985 [LU] Luxembourg ............... 85726

[51] Int. Cl.⁴ .............. C07C 69/76; A61K 7/06; A61K 31/33; A61K 31/70

[52] U.S. Cl. ............... 514/54; 562/405; 562/490; 514/844; 514/859; 514/863; 514/864; 514/880; 536/1.1; 536/4.1

[58] Field of Search ............ 562/405, 490; 514/54; 536/1.1, 4.1

[56] References Cited

U.S. PATENT DOCUMENTS 3,932,512 1/1976 Bharucha et al. ............ 514/888
4,454,341 6/1984 Dawson et al. ............... 562/490

FOREIGN PATENT DOCUMENTS 0002742 12/1978 European Pat. Off. .
0021339 6/1980 European Pat. Off. .

Primary Examiner—Ronald W. Griffin
Attorney, Agent, or Firm—Cushman, Darby & Cushman

[57] ABSTRACT

The invention relates to a compound of formula (I)

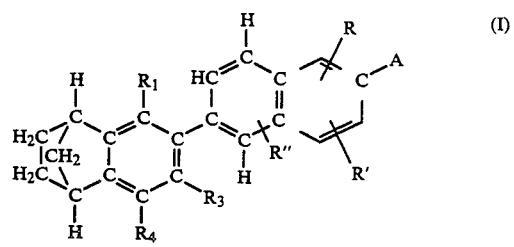

in which formula:

$R_1$, $R_3$ and $R_4$ denote, independently of each other a hydrogen atom, a $C_1$-$C_8$ alkyl radical, a $C_1$-$C_8$ alkoxy radical, a $C_1$-$C_8$ acryloxy radical or a hydroxy radical;

R, R' and R" denote, independently of each other, either one of the meanings given above for $R_1$, $R_3$ and $R_4$, or a halogen atom, or a primary, secondary or tertiary amino radical, A having various meanings.

The invention also relates to a process for the preparation of compounds of formula (I) and to medicinal and cosmetic compositions in which they are present.

34 Claims, No Drawings

BENZONORBORNENE DERIVATIVES PROCESS, FOR THEIR PREPARATION AND MEDICINAL AND COSMETIC COMPOSITIONS COMPRISED THEREOF

The invention relates to new chemical compounds consisting of benzonorbornenes substituted on one of the carbon atoms in the benzene ring, and, on the one hand, the preparation process enabling these new compounds to be obtained and, on the other hand, the use of these new compounds in cosmetic compositions or in pharmaceutical preparations for the treatment of dermatological complaints related to a keratinization (differentiation-proliferation) disorder, and for the treatment of dermatological or other complaints with an inflammatory and/or immuno-alergic component.

In addition, these compoounds can be used in the treatment of cutaneous or respiratory atopy.

The therapeutic action of vitamin A in its acid, aldehyde or alcohol form is well known in dermatology (see, on this subject, the publication Experientia, volume 34, pages 1105-1119 (1978)); this action in the treatment of cutaneous proliferations, of acne, of psoriasis and of similar complaints will be referred to hereinafter by the expression "differinic-type action". It has been found that products with a structure similar to that of vitamin A also had a differinic type action, but that the secondary effect of toxic hypervitaminosis could, in the case of some compounds, be multiplied by a lower factor than the multiplication factor of the required differinic effect (see, on this subject, Eur. J. Med. Chem.-Chimica Therapeutica, January-February 1980, 15, No. 1, pages 9-15); thus, French Patent Application Nos. 2,422,620 and 2,529,458 describe new stilbene and methylstyrylnaphthalene derivatives incorporating, on the ring on which an unsaturated substituent chain is grafted, a number of methyl groups, because the studies carried out led to the conclusion that multiplication of the methyl groups appeared to improve the therapeutic effectiveness (see the above-mentioned publication Eur. J. Med. Chem.).

Benzonorbornene and some of its derivatives were already known (see. on this subject, J. Org. Chem., 32, pages 893-901 (1967) and J. Am. Chem. Soc., 87: 21, pages 4794-4804 (1965)), but it had never been demonstrated that these benzonorbornene derivatives could have a differinic-type action. Subsequently, it has been shown that some norbornene derivatives had a differinic type of activity (see, on this subject, the publication J. Med. Chem. 1980, 23, pages 1013-1022 and 1981, 24, pages 1214-1223). However, in endeavoring to improve therapeutic effectiveness, the person skilled in the art, knowing that it was necessary to increase the methyl substitutions on this ring, tended to move away from benzonorbornene derivatives. Now, it has been found, according to the invention, that, surprisingly, some benzonorbornene derivatives have a particularly advantageous differinic-type action. In addition, the compounds according to the invention have, as a result of their structure, good stability to light and oxygen.

In view of their chemical structure and of their biological activity, the naphthalene derivatives of benzonorbornene according to the invention are referred to by the name of "naphthodifferins".

The invention consequently relates to the new industrial product consisting of a new chemical compound derived from benzonorbornene, corresponding to the formula (I):

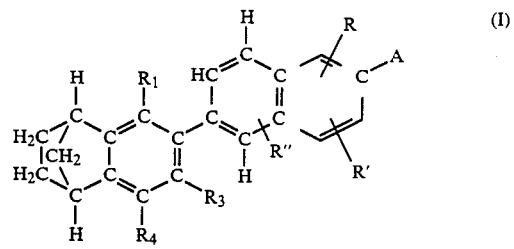

in which formula:

$R_1$, $R_3$, and $R_4$ denote, independently of each other, a hydrogen atom, a $C_1$-$C_8$ alkyl radical, a $C_1$-$C_8$ alkoxy radical, a $C_1$-$C_8$ acyloxy radical or a hydroxy radical;

R, R' and R" denote, independently of each other, either one of the meanings given above for $R_1$, $R_3$ and $R_4$, or a halogen atom, or a primary, secondary or tertiary amino radical;

A denotes H, OH, a $C_1$-$C_6$ alkyl radical, a $C_1$-$C_6$ alkoxy radical, a $CH_2OR_5$ group, in which $R_5$ denotes a hydrogen atom or a $C_1$-$C_6$ alkyl radical, a mono or polyhydroxy $C_2$ to $C_6$ alkyl, a $COR_6$ group in which $R_6$ denotes a hydrogen atom or a $C_1$-$C_6$ alkoxy, aryloxy, or benzyloxy radical, a sugar residue, a substituted or unsubstituted amino, $C_1$-$C_6$ alkyl or a hydroxy radical; and the corresponding salts.

A subgroup of compounds of the formula I of particular interest are the compounds of the formula IA

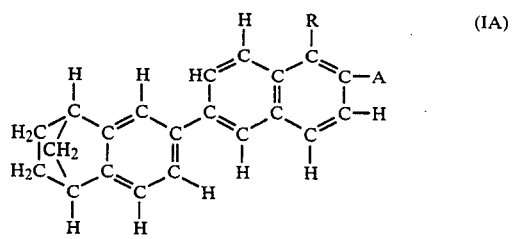

in which R is $C_1$ to $C_8$ alkyl and A is a group —$COR_6$ in which $R_6$ is an alkoxy of 1 to 6 carbon atoms, aryloxy, benzyloxy, a sugar residue, a substituted or unsubstituted amino or hydroxyl; and salts thereof.

When A denotes a $COR_6$ group and when $R_6$ denotes a $C_1$-$C_6$ alkoxy radical, it is preferable that $R_6$ is an $OR_7$ radical, $R_7$ being chosen from the group consisting of methyl, ethyl, propyl, butyl and hexyl radicals or of a $C_2$-$C_6$ alkyl radical substituted by one or more hydroxy radicals and, especially, 2-hydroxyethyl, 2-hydroxypropyl, or the isomers of dihydroxypropyl, such as 2,3-dihydroxypropyl, 1,3-dihydroxy-2-propyl or a pentaerythritol residue.

When A is a $COR_6$ group and when $R_6$ is an aryloxy radical, the aryl radical of $R_6$ can advantageously correspond to the formula (II):

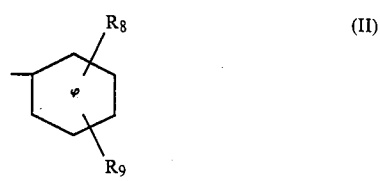

in which formula $R_8$ and $R_9$ denote, independently of each other, a hydrogen atom, a $C_1$–$C_4$ alkyl or a hydroxy radical, a halogen atom, a carboxyl group or a trifluoromethyl group.

When A is a $COR_6$ group and when $R_6$ is a benzyloxy radical, the benzyl radical of $R_6$ can advantageously correspond to the formula (III):

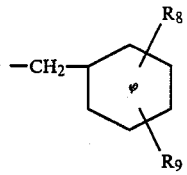

(III)

in which formula $R_8$ and $R_9$ have the same meanings as in the formula (II).

When A is a $COR_6$ group and when $R_6$ is a sugar residue, $COR_6$ is advantageously derived from a glucose ester, a mannitol ester or an erythritol ester.

When A is a $COR_6$ group and when $R_6$ denotes an amino radical of formula $NR_{10}R_{11}$, $R_{10}$ and $R_{11}$ can advantageously denote, independently of each other, a hydrogen atom, a straight-chain or branched $C_1$–$C_6$ alkyl radical, substituted or unsubstituted by one or more hydroxyl radicals, or they can also form a substituted or unsubstituted heterocyclic ring, one of the two radicals $R_{10}$ or $R_{11}$ being also capable, when the other is a hydrogen atom, of being an aryl radical of formula (II) or a benzyl radical of formula (III), in which formulae $R_8$ and $R_9$ have the meanings indicated above. Lastly, $NR_{10}R_{11}$ can correspond to the amine function of an amino acid or to the amine function of a glucosamine.

The invention also relates to a process for preparing the new compounds of formula (I), characterized in that, in a first step, the compound of formula (IV):

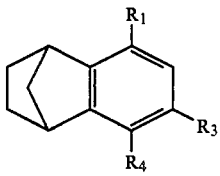

(IV)

where $R_1$, $R_3$ and $R_4$ have the meanings indicated earlier, is prepared in a known manner; that, in a second step, the 2-bromobenzonorbornene is prepared by treating the compound of formula (IV) with N-bromosuccinimide in a mixture of water and sulphuric acid, to obtain the 2-bromobenzonorbornene of formula (V):

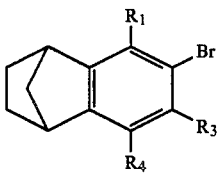

(V)

the meanings of the radicals $R_1$, $R_3$ and $R_4$ being those which were given previously; that the organomagnesium derivative of the compound of formula (V) is then prepared and that zinc chloride is reacted with the organomagnesium derivative thus prepared, to obtain the corresponding organozinc derivative; that, in a third step, a compound of formula (VI):

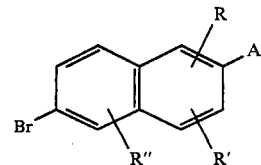

(VI)

where A, R, R' and R" have the meanings given previously, is prepared, in a known manner; and that, in a fourth step, the organozinc derivative obtained in the second step is coupled with the compound of formula (VI) in the presence of a palladium or nickel catalyst to obtain the compound of formula (I).

It should be stated that the synthesis of the compounds of formula (IV), which forms the first step of the preparation process according to the invention, has already been described in the case where $R_1$=$R_3$=$R_4$=H, in Lexemburg Patent Application No. 85,531, filed on Sept. 5, 1984, and in the case where $R_1$, $R_3$ and $R_4$ are other than hydrogen, in Luxemburg Patent Application No. 85,700, filed on Dec. 20, 1984.

It should also be stated that the first reaction carried out in the second step of the process specified above is a surprising synthesis.

According to the invention it has been found that the compounds of formula (I) have a differinic-type action and are particularly suitable for treating the dermatological complaints related to a keratinization (differentiation-proliferation) disorder, and dermatological or other complaints with inflammatory and/or immunoallergic components, particularly for treating common, comedonian or polymorphous acnes, senile or solar acnes, medicamentous or occupational acnes, extensive and/or severe forms of psiorasis and other keratinization disorders, particularly ichthyosis and ichthyosiform states, Darier's disease, palmo-planter keratosis, leukoplakias and leukoplakiform states, lichen planus, and all benign or malignant, severe or extensive dermatological proliferations; they are also active against some rheumatoidal complaints, especially rheumatoid psiorasis. They also find an application in the treatment of cutaneous or respiratory atopy. As a result, the invention also covers medicinal compositions in which the compounds of formula (I) are present.

The present invention consequently also relates to a new medicinal composition, intended particularly for the treatment of the abovementioned complaints, characterized in that it comprises, in a pharmaceutically acceptable base, at least one compound of formula (I) and/or its corresponding salts.

It is observed that the compounds of formula (I) have a good activity over a very wide range of diutions; in particular, concentrations of active compound(s) ranging from 0.0005% to 2% by weight can be used. It is possible, of course, to employ higher concentrations when this is required for a particular therapeutic application; however, the preferred concentrations of active principle are between 0.01 and 1% by weight.

When the compounds according to the invention are employed by topical administration, they are advantageously in the form of ointments, salves, tinctures, creams, emulsions, solutions, lotions, sprays, gels, suspensions, powders, adhesive patches or saturated pads. The compounds according to the invention are mixed with inert, non-toxic, generally liquid or pasty bases which are suitable for treatment by a topical route.

Solutions containing approximately 0.001%–0.3% by weight of active substance(s), or creams containing approximately 0.002%–0.5% of active substance(s) may advantageously be employed.

The compounds of formula (I) may be employed by an enteral route. By the oral route, the compounds of formula (I) are administered in a proportion of approximately 2 µg up to 2 mg per day and per kg of body weight; an excessive dosage may appear in the form of a hypervitaminosis A, recognizable by its symptoms and capable of suggesting a hepatic toxicity requring a biological control of the hepatic function. The required dosage may be administered as one or more doses. For administration by the oral route, the suitable forms are, for example, tablets, gelatine capsules, coated pills, syrups, suspensions, solutions, powders, granules or emulsions; a preferred mode of administration consists in using gelatine capsules containing from 0.1 mg to approximately 1 mg of active substance(s).

The compounds of formula (I) may also be administered by parenteral route in the form of solutions or suspensions for perfusions or intravenous or intramuscular injections. In this case, the compounds of formula (I) are advantageously administered in a dosage of approximately 2 µg up to 2 mg per day and per kg of body weight; in general, parenteral administration is carried out in a proportion of 0.01 mg to 1 mg of active substance(s) per ml.

Depending on the forms employed, the pharmaceutically acceptable base can contain, for example, water, gelatine, lactose, starch, talc, petroleum jelly, gum arabic, polyalkylene glycols, and magnesium stearate. The tablets, powders, granules, coated tablets or gelatine capsules may contain binders, fillers or pulverulent bases; the solutions or suspensions may contain diluents, solvents or thickeners.

In the treatment of keratinization disorders, the compounds of formula (I) employed in the medicinal compositions according to the invention act by increasing the epithelial follicular production of nonadherent cells, thus dislodging and expelling the contents of the acne comedon. These compounds reduce the size of the sebaceous glands and partly inhibit the secretion of sebum.

The compounds of formula (I) according to the invention also find an application in the cosmetic field, in particular in body hygiene and hair care and, in particular, for the treatment of skin susceptible to acne, for regrowth of hair, for combating hair loss, for combating the oily appearance of the skin or hair, for protection against the harmful effects of sunlight or for treating physiologically dry skins.

The present invention consequently also provides a cosmetic composition containing, in a cosmetically acceptable base, at least one compound of formula (I) or one of its salts this composition being in particular in the form of a lotion, gel, cream, soap or shampoo.

The concentration of compound(s) of formula (I) in these cosmetic compositions is between 0.0005% and 2% by weight and, preferably, between 0.01% and 1% by weight relative to the total weight of the composition.

The compositions according to the invention may contain inert or even pharmacodynamically or cosmetically active additives and, in particular, hydrating agents such as thiamorpholinone and its derivatives, or urea; antiseborrhoeic agents, such as 5-carboxymethylcysteine, 5-benzylcysteamine and their salts and their derivatives, or tioxolone; anti-acne agents such as benzoyl peroxide; antibiotics such as erythromycin neomycin and its esters or tetracyclines or 4,5-polymethylene 3-isothiazolines; agents promoting the regrowth of hair, such as Minoxidil (2,4-diamino-6-piperidinopyrimidine 3-oxide) and its derivatives, Diazoxide (7-chloro-3-methyl-1,2,4-benzothiadiazine-1,1-dioxide) and Phenytoin (5,5-dipheny imidazolidine-2,4-dione); steroid and nonsteroid antiinflammatory agents; carotenoids and, in particular, β-carotene; anitpsoriatic agents such as anthralin and its derivatives, and eicosa-5,8,11,14-tetraynoic and -5,8,11-triynoic acids, their salts and their amides.

The compositions according to the invention can also contain flavor-improving agents, preserving agents, stabilizers, moisture-controlling agents, pH-controlling agents, agents modifying osmotic pressure, emulsifying agents, UV-A and UV-B screens and antioxidants such as α-tocopherol, butylated hydroxylanisole or butylated hydroxytoluene.

To make the subject of the invention better understood, a description will now be given of several examples of implementation.

Details of the preparation of two compounds of formula (V) are given in Examples A and B which follow.

EXAMPLE A

Preparation of 2-bromobenzonorbornene (compound of formula (V) in which $R_1=R_3=R_4=H$)

10 g of N-bromosuccinimide are added in small portions over approximately two hours to a mixture of 5 g of benzonorbornene, stirred into 10 cm³ of water and 10 cm³ of sulphuric acid and heated to a temperature between 50° C. and 55° C. The progress of the reaction is followed by gas phase chromatography. When the benzonorbornene has been completely converted, the reaction mixture, at room temperature, is extracted with methylene chloride. The organic phase is washed with sodium bicarbonate until the pH of the washings is neutral and is then dried over magnesium sulphate and concentrated. 7 g of crude 2-bromobenzonorbornene are obtained and purified by distillation under reduced pressure. After distillation, 4 g of pure product are obtained. This product is a light-yellow liquid whose boiling point is 70°–75° C. at a pressure of approximately 2.65 10$^{-5}$ bar. Its proton nuclear magnetic resonance spectrum corresponds to the 2-bromobenzonorbornene structure.

EXAMPLE B

Preparation of 2-bromo-3-ethylbenzonorbornene (compound of formula (V) in which $R_1=R_4=H$ and $R_3=C_2H_5$)

8 g of 2-ethylbenzonorbornene in a mixture of 40 cm³ of water and 40 cm³ of sulphuric acid are treated with 15 g of N-bromosuccinimide in the same manner as in Example A, at a temperature between 50° C. and 55° C.

When all the starting material has been converted, after extraction of the reaction medium, the organic phase is washed with potassium bicarbonate, dried over magnesium sulphate and concentrated. 8 g of a crude product are obtained and purified by chromatography on a column of silica gel. After the elution phases have been evaporated down, 4 g of 2-bromo-3-ethylbenzonorbornene are obtained. This is a liquid whose purity and structure are verified by gas phase chromatography and by the proton nuclear magnetic resonance spectrum.

EXAMPLE 1

Preparation of methyl 6-[2-(5,8-methano-5,6,7,8-tetrahydronaphthyl)]naphthalene-2-carboxylate A solution of 4 g of 2-bromobenzonorbornene (0.018 mole) in 40 cm$^3$ of dry tetrahydrofuran (THF) is prepared. A crystal of iodine and 0.650 g of magnesium (0.027 mole) are added at ambient temperature to this solution, stirred under an argon atmosphere. The formation of the organomagnesium derivative is initiated by localized heating of the reaction mixture. The latter is then heated so that the THF refluxes.

The conversion of 2-bromobenzonorbornene is followed by gas phase chromatography. After two hours' heating, all the 2-bromobenzonorbornene has been converted to the corresponding magnesium derivative.

2.45 g of anhydrous zinc chloride (0.018 mole) are then added at ambient temperature. The reaction is exothermic. The temperature rises up to 50° C. and a greyish-white precipitate forms. Stirring is continued for an hour.

The reaction mixture is then cooled to 0° C., at which temperature 2.40 g of methyl 6-bromonaphthalene-2-carboxylate (0.009 mole) and 100 mg of a catalyst containing nickel chloride and diphenylphosphonoethane are added directly. The reaction mixture is diluted by adding 40 cm$^3$ of additional THF, and left stirred overnight.

The mixture is then hydrolyzed and then extracted several times with ethyl acetate. The extraction phases are combined, washed with water, dried over magnesium sulphate and concentrated. The expected crude product is crystallized from acetonitrile. In this manner, 2 g of methyl 6-[2-(5,8-methano-5,6,7,8-tetrahydronaphthyl)]naphthalene-2-carboxylate are obtained. The proton nuclear magnetic spectrum corresponds to the expected structure. The material is a white solid whose melting point is 107° C.

EXAMPLE 2

Preparation of methyl 6-[2-(3-ethyl-5,8-methano-5,6,7,8-tetrahydronaphthyl)]-2-carboxylate The operating conditions employed are the same as those in Example 1.

2-Bromo-3-ethylbenzonorbornene (3.7 g; 0.015 mole) is treated with 0.6 g of magnesium. The organomagnesium derivative is then converted to the corresponding zinc derivative by adding 2.5 g of anhydrous zinc chloride. When the exchange is complete, 2.4 g of methyl 6-bromonaphthalene-2-carboxylate (0.009 mole) are then added, together with 0.10 g of a catalyst containing nickel chloride and diphenylphosphonoethane.

When the reaction is complete, the mixture is hydrolyzed and then extracted several times with ethyl acetate. The organic phase is washed until the pH of the washings is neutral, is dried over magnesium sulphate and is then concentrated. The crude product obtained is recrystallized from acetonitrile.

1.8 g of methyl 6-[2-(3-ethyl-5,8-methano-5,6,7,8-tetrahydronaphthyl)]naphthalene-2-carboxylate are obtained in the form of white crystals melting at 116°–117° C.

The expected structure is confirmed by a proton nuclear magnetic resonance spectrum.

EXAMPLE 3

Preparation of 6-[2-(5,8-methano-5,6,7,8-tetrahydronaphthyl)]naphthalene-2-carboxylic acid A suspension of 1 g of the ester prepared according to Example 1 in 25 cm$^3$ of ethanol and 25 cm$^3$ of 6N potassium hydroxide is prepared. This stirred suspension is heated to a temperature between 50° and 60° C. After three hours, a homogeneous solution is obtained. At this stage, thin layer chromatography is used to check that all the starting material has been converted. The reaction mixture is then poured into 250 cm$^3$ of water and acidified by adding 5N hydrochloric acid. The expected acid precipitates in the form of a white solid. It is filtered off, dried and analysed. 0.9 g of 6-[2-(5,8-methano-5,6,7,8-tetrahydronaphthyl)]naphthalene-2-carboxylic acid is obtained. It is in the form of white crystals which have a melting point of 261° C.

The mass spectrum m/e=314 and the $^1$H and $^{13}$C nuclear magnetic resonance spectra are consistent with the structure.

EXAMPLE 4

Preparation of 6-[2-(3-ethyl-5,8-methano-5,6,7,8-tetrahydronaphthyl)]naphthalene-2-carboxylic acid 1 g of methyl 6-[2-(3-ethyl-5,8-methano-5,6,7,8-tetrahydronaphthyl)]naphthalene-2-carboxylate, prepared according to Example 2, is treated with an excess of potassium hydroxide using the same method as in Example 3. When all the ester has been converted into its potassium salt, the mixture is diluted with 200 cm$^3$ of water and acidified to a pH of about 1.5.

The exected acid precipitates; it is filtered off and dried.

0.85 g of white crystals with a melting point of 258° C. is obtained. The nuclear magnetic resonance spectrum ($^1$H, 250 MHz) confirms the expected structure.

The elemental analysis of the product obtained gives the following results:

|  | C | H | O |
| --- | --- | --- | --- |
| Calculated for $C_{24}H_{22}O_2$ | 84.17 | 6.47 | 9.34 |
| Found | 84.21 | 6.49 | 9.29 |

EXAMPLE 5

Preparation of N-ethyl-6-[2-(5,8-methano-5,6,7,8-tetrahydronaphthyl)]naphthalene-2-carboxyamide 2.5 cm$^3$ of dicyclohexylamine are added dropwise to a suspension of 3.7 g (0.012 mole) of the acid described in Example 3 in approximately 75 cm$^3$ of dry diethyl ether. The acid dissolves and after 10 minutes a white precipitate appears, which is filtered off, washed with ether and dried.

5 g (0.01 mole) of this salt are dissolved, under nitrogen, in approximately 75 cm$^3$ of dry dichloromethane and a solution of 0.75 cm$^3$ of thionyl chloride in 2 cm$^3$ of dichloromethane is added dropwise. After checking that the acid has been completely converted into the corresponding chloride, this solution is poured onto 25 cm$^3$ of aqueous ethylamine (40%). After 30 minutes the organic phase is separated off, washed with a dilute solution of hydrochloric acid, dried over magnesium sulphate and concentrated under reduced pressure. 2.6 g of the expected product are recovered and recrystallized from acetonitrile. The nuclear magnetic resonance spectrum ($^1$H, 250 MHz) corresponds to the expected structure.

The melting point is 149°-150° C.

The elemental analysis of the product obtained gives the following results:

|  | C | H | N | O |
|---|---|---|---|---|
| Calculated for $C_{14}H_{23}NO$ | 84.42 | 6.78 | 4.10 | 4.68 |
| Found | 84.28 | 6.78 | 4.02 | 4.90 |

EXAMPLE 6

The following composition is prepared:

| Compound of Example 3 | 0.010 g |
|---|---|
| Glycerine | 0.200 g |
| Sucrose | 0.050 g |
| Polyethylene glycol (average molecular weight: 400) | 0.050 g |
| Purified water q.s. | 0.400 g |

A suspension is thus obtained, which is packaged in a 0.4 g capsule consisting of gelatine, glycerine, titanium dioxide and water. This preparation is administered twice daily; good results are obtained within a period of 1 to 3 months, depending on the case of lichen planus treated.

EXAMPLE 7

The following composition is prepared:

| Compound of Example 3 | 0.002 g |
|---|---|
| Starch | 0.113 g |
| Dicalcium phosphate | 0.020 g |
| Silica | 0.020 g |
| Lactose | 0.030 g |
| Talc | 0.010 g |
| Magnesium stearate | 0.005 g |

A 0.2 g tablet is thus obtained. This tablet is to be taken twice daily for the treatment of psoriasis, and a significant improvement is found after three months.

EXAMPLE 8

The following composition is prepared:

| Compound of Example 5 | 0.002 g |
|---|---|
| Glycerine | 0.500 g |
| Sorbitol (70% strength) | 0.500 g |
| Sodium saccharinate | 0.010 g |
| Methyl para-hydroxybenzoate | 0.040 g |
| Flavering q.s. |  |
| Purified water q.s. | 5.000 ml |

A drinkable suspension is thus obtained, which is packaged in 5-ml vials. This drinkable suspension is used for the treatment of cases of palmo-planter keratosis by being ingested one to three times daily; a significant improvement is obtained after 1 to 3 months.

EXAMPLE 9

The following composition is prepared:

| Compound of Example 5 | 0.100 g |
|---|---|
| Cetyl alcohol | 3.000 g |
| Stearyl alcohol | 3.400 g |
| Cetyl alcohol oxyethylenated with 20 moles of ethylene oxide | 0.630 g |
| Stearyl alcohol oxyethylenated with 20 moles of ethylene oxide | 1.470 g |
| Glycerol monostearate | 2.000 g |
| Paraffin oil | 15.000 g |
| Glycerine | 10.000 g |
| Preserving agents q.s. |  |
| Distilled water q.s. | 100.000 g |

A nonionic suspension which forms an oil-in-water cream is thus obtained. This cream is used for the topical treatment of ichtyosis and is applied once to four times daily; good results are obtained within a period of two to three months.

EXAMPLE 10

The following composition is obtained:

| Compound of Example 3 | 0.010 g |
|---|---|
| Hydroxypropyl cellulose sold under the name "Klucel HF" by the Hercules Company | 2.000 g |
| Water/ethanol (50/50) q.s. | 100.000 g |

A gel is thus obtained, which is used for the treatment of acne and seborrhoea and is applied once to four times daily; good results are obtained within a period of one to three months, depending on the cases.

We claim:

1. A compound of formula (I)

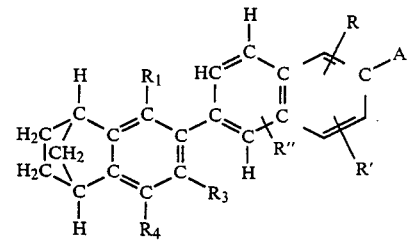

wherein $R_1$, $R_3$ and $R_4$ are the same or different and each is hydrogen, ($C_1$-$C_8$) alkyl, ($C_1$-$C_8$) alkoxy, ($C_1$-$C_8$) acyloxy or hydroxy;

R, R' and R'' are the same or different and each is hydrogen, halogen, ($C_1$-$C_8$) alkyl, ($C_1$-$C_8$) alkoxy, ($C_1$-$C_8$) acyloxy, hydroxy or primary, secondary or tertiary amino;

A is hydrogen, hydroxy, ($C_1$-$C_6$) alkyl, ($C_1$-$C_6$) alkoxy, mono or polyhydroxy ($C_2$-$C_6$) alkyl, a group —$CH_2OR_5$ in which $R_5$ is hydrogen or ($C_1$-$C_6$) alkyl or a group —$COR_6$ in which $R_6$ is hydrogen, ($C_1$-$C_6$) alkoxy, aryloxy, benzyloxy, sugar residue, substituted or unsubstituted amino, ($C_1$-$C_6$)alkyl or hydroxy, or a salt thereof.

2. A compound according to claim 1 wherein A is a group —$COR_6$ and $R_6$ is a group $OR_7$ and $R_7$ is methyl, ethyl, propyl, butyl or hexyl or ($C_2$-$C_6$) alkyl bearing one or more hydroxy substituents.

3. A compound according to claim 1 wherein a is a group —$COR_6$ and $R_6$ is aryloxy in which the aryl radical is a group of formula (II)

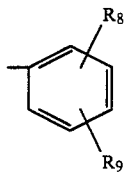

wherein $R_8$ and $R_9$ are the same or different and each is hydrogen, ($C_1$-$C_4$) alkyl, hydroxy, halogen, carboxyl or trifluoromethyl.

4. A compound according to claim 1 wherein A is a group —$COR_6$ and $R_6$ is benzyloxy in which the benzyl radical is a group of formula (III)

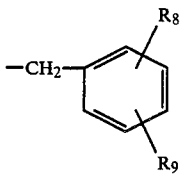

wherein $R_8$ and $R_9$ are the same or different and each is hydrogen, ($C_1$-$C_4$) alkyl, hydroxy, halogen, carboxyl or trifluoromethyl.

5. A compound according to claim 1 wherein A is a group —$COR_6$ and $R_6$ is a sugar residue and the group —$COR_6$ is derived from a glucose ester, a mannitol ester or an erythritol ester.

6. A compound according to claim 1 wherein A is a group —$COR_6$ and $R_6$ is a group —$NR_{10}R_{11}$ wherein $R_{10}$ and $R_{11}$ are the same or different and each is hydrogen, straight- or branched-chain ($C_1$-$C_6$) alkyl which is unsubstituted or which bears one or more hydroxy substituents or $R_{10}$ and $R_{11}$ together form a substituted or unsubstituted heterocyclic ring, or one of $R_{10}$ and $R_{11}$ is hydrogen and the other is aryl of formula (II)

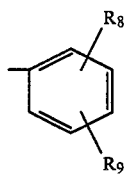

or a benzyl radical of formula (III)

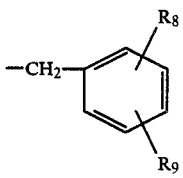

wherein $R_8$ and $R_9$ are the same or different and each is hydrogen, ($C_1$-$C_4$) alkyl, hydroxy, halogen, carboxyl or trifluoromethyl, or wherein the group $NR_{10}R_{11}$ is the amine function of an amino acid or the amine function of a glucosamine.

7. A compound according to claim 1 of the formula IA

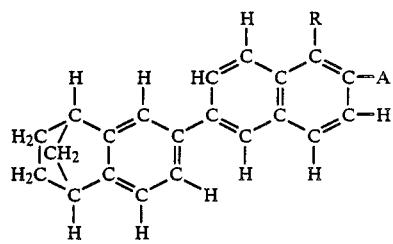

in which R is $C_1$-$C_8$ alkyl, A is a group —$COR_6$ in which $R_6$ is an alkoxy of 1 to 6 carbon atoms, aryloxy, benzyloxy, a sugar residue, a substituted or unsubstituted amino or hydroxy or a salt thereof.

8. A process for the preparation of a compound as defined in claim 1 comprising reacting the organozinc derivative of a compound of formula (V)

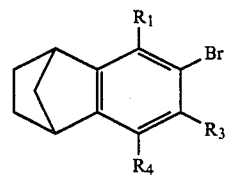

wherein $R_1$, $R_3$ and $R_4$ are as defined in claim 1, with a compound of formula (VI)

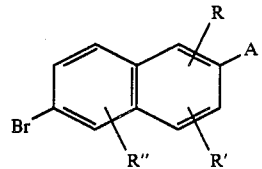

wherein A, R, R' and R" are as defined in claim 1 in the presence of a palladium or nickel catalyst.

9. A process according to claim 8 wherein the organozinc derivative of the compound of formula (V) is prepared by reacting the organomagnesium derivative of a compound of formula (V) with zinc chloride, the organomagnesium derivative of the compound of formula (V) is prepared by reacting a compound of formula (V) with magnesium, the compound of formula (V) is prepared by reacting a compound of formula (IV)

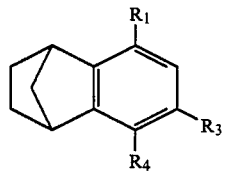

wherein $R_1$, $R_3$ and $R_4$ are as in claim 1 with N-bromosuccinimide in a mixture of water and sulphuric acid.

10. A composition comprising an effective amount of at least one compound of formula (I) as defined in claim 1 in a pharmaceutically acceptable base.

11. A composition according to claim 10, comprising from 0.0005 to 2% by weight of the compound of formula (I).

12. A composition according to claim 11 comprising from 0.01 to 1% by weight of the compounds of formula (I).

13. A composition according to claim 10, formulated for topical administration in the form of an ointment, gel, cream, salve, powder, tincture, solution, suspension, emulsion, lotion, spray, adhesive patch or a saturated pad.

14. A composition according to claim 13 formulated as a solution comprising from 0.001% to 0.3% by weight of the compounds of formula (I).

15. A composition according to claim 13 formulated as a cream comprising from 0.002% to 0.5% by weight of the compounds of formula (I).

16. A composition according to claim 10, formulated for enteral administration.

17. A composition according to claim 10, formulated as a solution or suspension for parenteral administration.

18. A composition according to claim 17, comprising from 0.01 to 1 mg of the compounds of formula (I) per ml of solution or suspension.

19. A composition according to claim 10, comprising at leat one inert or pharmacodynamically or cosmetically active additives.

20. A composition according to claim 19 wherein the additive is a hydrating agent, antiseborrhoeic agent, antibiotic agent promoting regrowth of hair, antiinflammatory agent, carotenoid, antpsorietic agent, flavouring agent, preserving agent, stabilizer, moisture-regulating agent, pH-regulating agent, agent modifying osmotic pressure, emulsifier, UV-A or UV-B screen or antioxidant.

21. A composition according to claim 10 wherein the pharmaceutically acceptable base comprises at least one component selected from a diluent, a solvent, a thickener, a binder and a filler.

22. The composition of claim 21 wherein said at least one component is water, gelatin, lactose, starch, talc, petrolatum jelly, gum arabic, polyalkylene glycol or magnesium stearate.

23. A cosmetic composition comprising at least one compound of formula (I) as defined in claim 1 in a cosmetically acceptable base.

24. A composition according to claim 23 comprising from 0.0005 to 2% by weight of the compound of formula (I).

25. A composition according to claim 24 comprising from 0.01 to 1% by weight of the compound of formula (I).

26. A composition according to claim 23, presented as a lotion, gel, cream, soap or shampoo.

27. A method for treating the human or animal body comprising administering a compound of formula (I) as defined in claim 1 to a human or animal in need thereof.

28. A method according to claim 27 for the treatment of dermatological complaints.

29. A method according to claim 28 for the treatment of keratinization (differentiation-proliferation) disorder.

30. A method according to claim 27 for the treatment of inflammatory or immuno-allergic conditions.

31. A method according to claim 27 for the treatment of acnes, ichthyosis and ichthyosiform states, Darier's disease, palmoplanter keratosis, leukoplakia and leukoplaki-form states, all benign or malignant dermatological proliferations, lichen and psoriasis, cutaneous or respiratory atopies, and rheumatoidal complaints.

32. A method according toclaim 27 for treatment by way of body hygiene, or hair care or for the treatment of skin susceptible to acne, seborrhoeas, hair loss, for the regrowth of hair, for protection against the harmful effects of sunlight or for the treatment of physiologically dry skins.

33. A method according to claim 27 wherein the compound of formula (I) is administered orally or parenterally in a dosage of from 2 $\mu$g to 2 mg per kg of body weight per day.

34. 6-[2-(5,8-methano-5,6,7,8-tetrahydro-naphthyl)]naphthalene-2-carboxylic acid.

* * * * *